(12) United States Patent
Samant et al.

(10) Patent No.: US 12,226,385 B2
(45) Date of Patent: Feb. 18, 2025

(54) SYNERGISTIC COMPOSITION FOR ACTIVATING INTRACELLULAR SECONDARY MESSENGER(cAMP) PATHWAY

(71) Applicant: CELAGENEX RESEARCH (INDIA) PRIVATE LTD., Maharashtra (IN)

(72) Inventors: Rajaram Samant, Thane (IN); Rajendra Prasad Tongra, Jaipur (IN); Jotiram Palkar, Thane (IN)

(73) Assignee: CELAGENEX RESEARCH (INDIA) PRIVATE LTD., Thane (IN)

( * ) Notice: Subject to any disclaimer, the term of this patent is extended or adjusted under 35 U.S.C. 154(b) by 0 days.

(21) Appl. No.: 17/840,532

(22) Filed: Jun. 14, 2022

(65) Prior Publication Data
US 2022/0313638 A1 Oct. 6, 2022

(30) Foreign Application Priority Data
Nov. 12, 2021 (IN) .............................. 202121051996

(51) Int. Cl.
A61K 31/197 (2006.01)
A61K 9/48 (2006.01)
A61K 31/155 (2006.01)
A61P 25/28 (2006.01)

(52) U.S. Cl.
CPC ............ *A61K 31/197* (2013.01); *A61K 9/485* (2013.01); *A61K 9/4858* (2013.01); *A61K 9/4866* (2013.01); *A61K 31/155* (2013.01); *A61P 25/28* (2018.01)

(58) Field of Classification Search
CPC .... A61K 31/197; A61K 9/485; A61K 9/4858; A61K 9/4866; A61K 31/155; A61K 9/2009; A61K 9/2013; A61K 9/2018; A61K 9/2027; A61K 9/2054; A61P 25/28
See application file for complete search history.

(56) References Cited

U.S. PATENT DOCUMENTS

| | | | |
|---|---|---|---|
| 5,677,349 A | 10/1997 | Gilad et al. | |
| 10,130,602 B2 | 11/2018 | Williams et al. | |
| 2004/0009926 A1* | 1/2004 | Pettegrew | A61K 31/7024 514/23 |
| 2009/0069331 A1 | 3/2009 | Vallance et al. | |
| 2018/0054348 A1 | 2/2018 | Luo et al. | |
| 2018/0303896 A1* | 10/2018 | Cross, III | A61K 31/385 |

FOREIGN PATENT DOCUMENTS

| | | |
|---|---|---|
| SG | 11201900269 A | 3/2019 |
| WO | 2002096411 A1 | 12/2002 |
| WO | 2006051314 A8 | 9/2006 |
| WO | 2007120096 A1 | 10/2007 |
| WO | 2018226732 A1 | 12/2018 |

OTHER PUBLICATIONS

Gad M. Gilad, Varda H. Gilad, Evidence for oral agmatine sulfate safety—A 95-day high dosage pilot study with rats, Food and Chemical Toxicology, 2013, 62:758-762. (Year: 2013).*
Remington, "Tablet Ingredients", Remington: The Science and Practice of Pharmacy, 21st Edition, Beringer et al. Editors, 2005, pp. 891-894. (Year: 2005).*
Kingchem, "N-Acetyl-L-Carnitine HCl", Kingchem.com, 2018, 4 pages, downloaded from "www.Kingchem.com/nutritional/n-acetyl-l-carnitine-hcl/" on Aug. 24, 2022. (Year: 2018).*
Chem Impex, "Agmatine sulfate", ChemImpex.com, 2018, 2 pages, downloaded from "www. chemimpex.com/agmatine-sulfate" on Aug. 23, 2022. (Year: 2018).*
Tanvi M. Deshpande, Anisul Quadir, Sakae Obara, Stephen W. Hoag. Impact of formulation excipients on the thermal, mechanical, and electrokinetic properties of hydroxypropyl methylcellulose acetate succinate (HPMCAS), International Journal of Pharmaceutics ,vol. 542, Issues 1-2, 2018, 132-141. (Year: 2018).*
Kalasz, H., & Antal, I. (2006). Drug excipients. Current Medicinal Chemistry, 13(21), 2535-63. (Year: 2006).*
Chou, T.C.,Cancer Res., 2010, 70(2), 440-446 (Year: 2010).*
Berenbaum. Clin. Exp. Immunol., 1977, 28, 1-18 (Year: 1977).*
Shopsin, B. (2013). The clinical antidepressant effect of exogenous agmatine is not reversed by parachlorophenylalanine: A pilot study. Acta Neuropsychiatrica, 25(2), 113-118. (Year: 2013).*
Keynan O, Mirovsky Y, Dekel S, Gilad VH, Gilad GM. Safety and Efficacy of Dietary Agmatine Sulfate in Lumbar Disc-associated Radiculopathy. An Open-label, Dose-escalating Study Followed by a Randomized, Double-blind, Placebo-controlled Trial. Pain Med. Mar. 2010; 11(3):356-68 (Year: 2010).*
Maia Pujara et al., "Mechanisms of Reward Circuit Dysfunction in Psychiatric Illness: Prefrontal-Striatal Interactions," The Neuroscientist, vol. 20, Issue 1, Aug. 7, 2013, pp. 82-95.
Salgado et al., "The Nucleus Accumbens: A Comprehensive Review," Stereotact Funct Neurosurg, vol. 93, Feb. 18, 2015, pp. 75-93.
Mavridis, "The role of the nucleus accumbens in psychiatric disorders," Psychiatriki, vol. 25, Issue No. 4, Oct.-Dec. 2015, pp. 282-294. English Abstract.

(Continued)

*Primary Examiner* — Matthew P Coughlin
*Assistant Examiner* — David M Shim
(74) *Attorney, Agent, or Firm* — Maschoff Brennan

(57) ABSTRACT

The invention discloses herein related to synergistic combination of exogenous bioactives for activating intracellular secondary messenger (cAMP) signalling pathway. Particularly, the invention relates to synergistic compositions comprising combination of therapeutically effective amount of (3R)-3-acetyloxy-4-(trimethylazaniumyl) butanoate and N-4-aminobutylguanidine and salts thereof present in a weight ratio of 1:0.01 to 1:2 along with pharmaceutically acceptable excipients. Furthermore, the composition is useful for treating disease conditions or disorders related to depletion of secondary messenger pathway. The present invention further provides method of treating disease conditions related mental illness or disorder.

2 Claims, 3 Drawing Sheets

(56) References Cited

OTHER PUBLICATIONS

Lee et al., "The indirect efect of peer problems on adolescent depression through nucleus accumbens volume alteration," Scientific Reports, vol. 10, Article No. 12870, Jul. 30, 2020, 9 pages.

Narayanaswamy, "Clinical correlates of nucleus accumbens volume in drug-naïve, adult patients with obsessive-compulsive disorder," Australian & New Zealand Journal of Psychiatry 47(10), Jun. 4, 2013 pp. 930-937.

Zhang et al., "Reduced Neuronal cAMP in the Nucleus Accumbens Damages Blood-Brain Barrier Integrity and Promotes Stress Vulnerability," vol. 87, Issue 6, Mar. 15, 2020, pp. 526-537.

Ferro, "Mechanistic target of rapamycin modulation: an emerging therapeutic approach in a wide variety of disease processes," Br J Clin Pharmacol. 82(5), Oct. 12, 2016, pp. 1156-1157.

Masi et al., "Effects of Long-Term Acetyl-L-Carnitine Administration in Rats—II: Protection Against the Disrupting Effect of Stress on the Acquisition of Appetitive Behavior," Neuropsychopharmacology, vol. 28, Oct. 1, 2002, pp. 683-693.

Valverde et al., "Agmatine as a novel candidate for rapid-onset antidepressant response," World J Psychiatry, vol. 11. Issue No. 11, Nov. 19, 2021, pp. 981-996.

Olescowicz et al., "Protective Effects of Agmatine Against Corticosterone-Induced Impairment on Hippocampal mTOR Signaling and Cell Death," Neurotoxicity Research, vol. 38, May 12, 2020, pp. 319-329.

Chen et al., "Evidence of Reduced Agmatine Concentrations in the Cerebral Cortex of Suicides," International Journal of Neuropsychopharmacology, vol. 21, Issue 10, Jul. 9, 2018, pp. 895-900.

Shopsin, "The clinical antidepressant effect of exogenous agmatine is not reversed by parachlorophenylalanine: a pilot study," Acta Neuropsychiatrica, Cambridge University Press, Feb. 26, 2013, abstract.

PCT International Search Report in Application No. PCT/IN2022/05044 Dated Sep. 16, 2022.

IN Office Action in Application No. 202121051996 Dated Jul. 14, 2022.

* cited by examiner

SYNERGISTIC COMPOSITION FOR ACTIVATING INTRACELLULAR SECONDARY MESSENGER(cAMP) PATHWAY

FIELD OF THE INVENTION

The present invention generally relates to synergistic combination of exogenous bioactives for activating intracellular secondary messenger (cAMP) signalling pathway.

Particularly, the invention relates to synergistic compositions comprising combination of therapeutically effective amount of (3R)-3-acetyloxy-4-(trimethylazaniumyl) butanoate and N-(4-aminobutyl) guanidine and salts thereof present in a specific ratio along with pharmaceutically acceptable excipients.

Furthermore, the composition of the present invention is useful for treating disease conditions or disorders related to depletion of secondary messenger pathway. The present invention further provides method of treating disease condition related mental illness or disorder.

BACKGROUND OF THE INVENTION

The human brain is an important organ of the human body. It has a complex structure, which contains billions of nerve cells (neurons). Neurons communicate and work together for the human body to function normally. These neurons of the brain communicate through electrical signals. There are special chemicals called neurotransmitters, which help to move these electrical signals from neuron to neuron. Most scientists suggest that mental illnesses result from problems with the communication between neurons in the brain (i.e., neurotransmission).

Mental illness also called mental health disorder further refers to a wide range of mental health problems that affect human mood, thinking and behaviour. Examples of mental illness include depression, anxiety disorders, schizophrenia and addictive behaviours. Many people have mental health concerns from time to time, but a mental health concern becomes a mental illness when ongoing signs and symptoms cause frequent stress and affect your ability to conduct daily functions.

Some leading causes of mental disability are major depression, bipolar disorder, schizophrenia, and obsessive-compulsive disorder, which are all mental illnesses. About three percent of the global population has more than one mental illness at a time.

Mental disorders were leading causes of the global health-related burden, with depressive and anxiety disorders being leading contributors to this burden. According to WHO depression is a common illness worldwide, with an estimated 3.8% of the population affected, including 5.0% among adults and 5.7% among adults older than 60 years. Approximately 280 million people in the world have depression. Over 700,000 people die due to suicide every year. Suicide is the fourth leading cause of death in 15-29-year-olds.

It is observed that rates of depression and anxiety climbed globally by more than 25% in 2020, a devastating ripple effect of the Covid-19 pandemic that has particularly affected women and young people.

The human brain's "reward circuit" has been widely implicated in the pathophysiology of mental illness. The human brain's "reward circuit" is the putative network of regions encoding various aspects of pleasure, motivation, value, and decision-making. The putative network is a major focus of research on the pathophysiology of mental illness. Past clinical neuroimaging studies have consistently identified abnormalities in reward circuit function across a range of psychiatric disorders, depression, schizophrenia, obsessive-compulsive disorder, autism, and attention deficit hyperactive disorder.

In a corresponding way of the research-work done on rodents, the ventral striatum of the brain has been shown to be essential part for mediating responses to rewards. Further, functional mapping studies have linked behavioural reward responses to a smaller subregion within the ventral striatum which is recognized as the nucleus accumbens (NAcc) (*Neuroscientist.* 2014 February; 20(1): 82-95).

The nucleus accumbens (NAcc) is found in an area of the brain called the basal forebrain. The nucleus accumbens (NAcc) is a part of the basal ganglia and it is the main component of the ventral striatum. The nucleus accumbens (NAcc) is a major component of the ventral striatum and has long been thought to be a key structure involved in mediating motivational and emotional processes, the limbic-motor interface, and the effects of certain psychoactive drugs. The NAcc has been implicated in numerous neurological and psychiatric disorders, including depression, obsessive-compulsive disorder, bipolar disorder, anxiety disorders, Parkinson's disease, Alzheimer's disease, Huntington's disease, obesity, in drug abuse and addiction (*Stereotact Funet Neurosurg* 2015:93:75-93).

The nucleus accumbens is playing a modulative role in the flow of information from the amygdaloid complex to these regions. Nucleus accumbens also has a role in other psychiatric disorders such as bipolar disorder, attention deficit/hyperactivity disorder and post-traumatic stress disorder. Neuromodulation interventions targeting the nucleus accumbens are nowadays applied in selected patients suffering from treatment-resistant depression, obsessive-compulsive disorder, Tourette syndrome and addiction to drugs or alcohol. Nucleus accumbens' deep brain stimulation has also been associated with antidepressant and anxiolytic effect, as well as quality of life improvement in patients suffering from severe resistant depression (*Psychiatriki.* October-December 2015; 25(4):282-94).

Further studies indicate that NAcc volume may be one possible structural alteration that plays an important role in linking peer problems as social stress with depression in adolescence. However, the indirect effects of peer problems on adolescent depression via the amygdala and hippocampal volumes were not significant. Major depressive disorder (MDD) adolescents showed larger NAcc volume (7.59%) compared to healthy controls (*Scientific Reports* (2020) 10:12870). The volumetric abnormalities of NAcc and its correlation with illness severity in drug-nave, adult patients with OCD is reported in article *Australian & New Zealand. Journal of Psychiatry* 47(10) 930-937. (2013).

Intriguingly it is found that cAMP levels were markedly decreased in neurons of the NAc, rather than in endothelial cells, astrocytes, or microglia. RNA-sequencing data showed that adenylate cyclase 5 (Adcy5), an enzyme responsible for the synthesis of cAMP from adenosine triphosphate (ATP), was predominantly expressed in the NAc; it also resided exclusively in neurons. Moreover, deficient neuronal cAMP production in the NAc decreased the expression of reelin, while supplementary injection of exogenous reelin into the NAc promoted BBB integrity and ameliorated depression-like behaviors. [*Biological Psychiatry* 87, 6, 2020, 526-537].

Further the transcription factor cAMP response element (CRE)-binding protein (CREB) has been shown to regulate neural plasticity Secondary messenger Cyclic AMP (cAMP) is a chemical second messenger that couples extracellular signals to intracellular responses in all cell types.

Cyclic AMP is a central player in the network of signalling pathways underlying pathogenesis of several diseases and several interference points are used therapeutically in a variety of conditions. Although the clinical impact of changes in cAMP remains incompletely defined, one fundamental conclusion can nevertheless be drawn: interventions that enhance cAMP generation or actions have potential to alleviate mood disorders.

cAMP has very rapid turnover as a result of a constant dynamic balance between its formation by adenylyl cyclase and conversion to AMP by phosphodiesterases (PDEs). Currently, the adenylyl cyclase activity has been mostly pharmacologically targeted through agonists or antagonists—affecting upstream G-protein-coupled receptors (GPCR) The cAMP-dependent protein kinase (protein kinase A [PKA]) is a central component of cAMP signalling cascade because, with few exceptions, the intracellular events mediated by cAMP occur through its activation.

Studies have suggested that chronic social stress specifically downregulates endothelial tight junction protein expression in the nucleus accumbens (NAc), thus increasing blood-brain barrier (BBB) permeability and promoting depression-like behaviors. However, the molecular mechanism underlying the reduction in tight junction protein, particularly in the NAc, is largely uncharacterized. Moreover, reduced neuronal camp in the nucleus accumbens damages blood-brain barrier integrity and promotes stress vulnerability [*Biol psychiatry.* 2020 Mar. 15; 87(6):526-537].

Classic antidepressants, such as escitalopram, paroxetine, and tranylcypromine, only increase levels of serotonin or monoamines. Ketamine, induce antidepressant-like effects in animals, rapidly by increasing mTOR signalling, brain derived neurotrophic factor (BDNF) levels, and structural and functional plasticity in the prefrontal cortex and hippocampus (B*r J Clin Pharmacol.* 2016 November; 82(5): 1280-1290).

Notably use of traditional anti-depressants (TADs) like Selective serotonin reuptake inhibitors (SSRIs), Serotonin and norepinephrine reuptake inhibitors (SNRIs), Tricyclic and tetracyclic antidepressants, Monoamine oxidase inhibitors (MAOIs) are accompanied with certain limitations.

Antidepressant polypharmacy is a type of multimodal treatment that needs to be compared to the use of a single antidepressant and a synergist. Multiple prescribers reduced patients' confidence in the treating physician, subsequently influencing their medication-taking behaviour. Further increased risk of relapse and recurrence where one third of patients reported an increase in symptom severity, as a result of discontinuing TADs.

The onset of effect is delayed (by 8-12 weeks), thus causing higher drop-outs, mistrust with clinician. There are high non-responder rates where more than 50% patients fail to respond to the first anti-depressant drug. High rate of relapse, poor response in early onset and or Female population. And also, high side effect (20%-40%) profile leading to poor patient compliance.

The present inventors with due research found that there is acute deficiency of c-AMP in patients with depression. TADs fail to increase c-AMP leading to non-responder rate. Typical antidepressants need secondary messenger (c-AMP) to increase synaptic proteins and synaptic function.

Hence, there is unmet need to find out therapeutic approach that regulate secondary messenger level that rapidly affect synaptic proteins BDNF, neuroplasticity and synaptogenesis in psychiatric patients.

In view of above, the inventors of the present invention have observed that acetylated form of L-carnitine is a well-known mitochondria-boosting supplement and has shown promising antidepressant effects and opened new therapeutic opportunities for restoring neurological and psychiatric disorders.

(3R)-3-acetyloxy-4-(trimethylazaniumyl)butanoate is made from L-carnitine. L-carnitine is a derivative of an amino acid. (3R)-3-acetyloxy-4-(trimethylazaniumyl) butanoate helps the body to produce energy. It is important for heart and brain function, muscle movement, and many other body processes. ALCAR is an endogenous metabolic intermediate that facilitates the influx and efflux of acetyl groups across the mitochondrial inner membrane.

WO2002096411 discloses use of an acetyl-L-carnitine, or a pharmaceutically acceptable salt thereof, for the preparation of a medicament for the treatment of anhedonia. Further it is reported that Long-term acetyl-L-carnitine (ALCAR) administration prevents the development of depression produced by acute exposure to unavoidable stress (Neuropsychopharmacology volume 28, pages 683-693 (2003)).

U.S. Pat. No. 10,130,602B2 discloses non-therapeutic use of L-carnitine, a salt of L-carnitine, a derivative of L-carnitine and/or a salt of a derivative of L-carnitine for reducing or preventing mental fatigue and/or for improving cognitive function in a non-elderly animal.

It is well established that cAMP is a derivative of adenosine triphosphate (ATP) and used for intracellular signal transduction in many different organisms, conveying the cAMP-dependent pathway. Cyclic adenosine monophosphate (cAMP) is a second messenger, which is synthesized from adenosine triphosphate (ATP) by enzymes (g-proteins) that are attached to metabotropic receptors and become released when the receptor is activated. Further the cAMP level is controlled by two types of enzymes: ACs and phosphodiesterases (PDE). ACs catalyse the production of cAMP from ATP, whereas PDEs control the rate of cAMP degradation to AMP.

ATP to cAMP conversion is catalyzed by the adenylyl cyclase, which required abundant ATP production. Acetyl-L-carnitine supplementation increases rates of overall ATP production. Remarkably the present inventors with extensive research found that (3R)-3-acetyloxy-4-(trimethylazaniumyl)butanoate role in cAMP enhancement is significant, however mere use of said compound is not enough to regulate different parameters which may affect cAMP level, like the hormonal factor.

It has been widely documented that there are gender differences in depression prevalence, with women experiencing major depression more often than men. The peak onset of depressive disorders in women coincides with their reproductive years (between the ages of 25 to 44 years of age), hormonal risk factors may play an important role.

Estrogen and progesterone have been shown to affect neurotransmitter, neuroendocrine, and circadian systems that have been implicated in mood disorders.

Most of the diseases occur after childbirth and during pregnancy or gestation period which can lead to severe problems such as postpartum depression (PPD), postmenopausal depression, perimenopausal depression which ultimately affects the mental health condition and develop various depressive episodes which ultimately lead to depression in women.

The blood-brain barrier (BBB), which saves the brain from toxic substances, is formed by endothelial cells. It is mainly composed of tight junction (TJ) proteins existing between endothelial cells. Estrogen is an important regulatory hormone of BBB permeability. The estrogen-reduction increase disruption in junctional protein levels like Claudin 5 proteins which may lead to impairment in vascular structural integrity and barrier function of vascular endothelium that leads to BBB leakiness. Leaky BBB— leads to increased inflammatory cytokines in CNS—hampering formation of synapse proteins.

Therefore, it is required to resolve the problems associated with leaky BBB due to hormonal dysregulation. Moreover, it is needed to target the root causes of female depression linked with the hormonal factors.

The inventors of present invention have developed a combination product where the factor or messenger get enhanced substantially in a subject in need thereof.

Moreover, the inventors have developed as synergistic combination where one ingredient acts exogenously and other act as endogenously to improve cAMP level.

The role of agmatine as A MPA activator, NMDA blocker, mTOR regulator for normal functioning of the central nervous system (CNS), including cognitive function, locomotion, and breathing known in the art.

Agmatine, an endogenous glutamatergic modulator, has been postulated to elicit fast behavioral and synaptogenic effects by stimulating the mechanistic target of rapamycin complex 1 signalling pathway, similar to ketamine [*World J Psychiatry*. 2021 Nov. 19; 11(11): 981-996].

Protective effects of agmatine against corticosterone-induced impairment on hippocampal mtor signalling and cell death is reported in the literature [Neurotox Res 2020 August; 38(2):319-329].

Agmatine was significantly reduced in the cortex of suicides, irrespective of meeting criteria for major depressive disorder compared with controls [Int J Neuropsychopharmacol. 2018 October; 21(10): 895-900].

Particularly it has been found that the antidepressant effect of exogenous agmatine was documented in a small number of MDD subjects, and was not reversed/modified by potent serotonin inhibitor confirming findings in animals that therapeutic response is not mediated by serotonergic mechanisms. (*Acta Neuropsychiatr.* 2013 April; 25(2):113-81.

Agmatine's recognized function in brain as inhibitory modulator of excitatory glutamatergic transmission suggests a pivotal role for brain glutamate, contributing to the ripening glutamatergic basis of depression, and a rational basis for future antidepressant pharmacotherapy.

The inventors of the present invention surprisingly found that (3R)-3-acetyloxy-4-(trimethylazaniumyl) butanoate in combination with N-(4-aminobutyl)guanidine not only activate cAMP level endogenously but also regulate hormonal imbalances Unprecedentedly the inventors have successfully established a synergistic theory wherein (3R)-3-acetyloxy-4-(trimethylazaniumyl) butanoate in specific ratio of N-(4-aminobutyl)guanidine improves cAMP level, with no severe adverse effect.

OBJECTIVE OF THE INVENTION

The primary objective of the invention is to provide synergistic compositions for activating intracellular secondary messenger (cAMP) pathway.

Another objective of the invention is to provide bioavailable, safe, non-toxic, rapid acting bioactive composition.

Yet another objective of the invention is to provide synergistic composition for treating psychiatric disorders through site specific action with no severe adverse effects.

SUMMARY OF THE INVENTION

To meet the above objectives, the inventors of the present invention performed experiments to establish significant effect of the active ingredients or minerals or amino acid derivatives or nutrients or bioactives present in the composition for treating mental illness in a subject in need thereof in safer way.

In an aspect, the invention relates to synergistic compositions comprising therapeutically active ingredients along with pharmaceutically acceptable carriers for activating intracellular secondary messenger (cAMP) pathway.

In another aspect, the invention relates to synergistic compositions comprising combination of bioactive ingredients, present in a specific weight ratio to normalize nucleus accumbens (NAcc) volumetric abnormalities by enhancing cAMP signalling pathway.

In another aspect, the present invention provides synergistic bioactive composition for treatment of neurological and psychiatric disorders comprising administration of effective dose of exogenous blend of (3R)-3-acetyloxy-4-(trimethylazaniumyl)butanoate and N-(4-Aminobutyl)guanidine along with pharmaceutically acceptable excipients.

In further aspect, the invention provides effective, rapid acting, synergistic composition of biologically active ingredients (3R)-3-acetyloxy-4-(trimethylazaniumyl)butanoate and N-(4-Aminobutyl)guanidine present in specific weigh ratio, wherein the exogenous (3R)-3-acetyloxy-4-(trimethylazaniumyl)butanoate improves the cAMP level, concurrently N-(4-Aminobutyl)guanidine increasing endogenous ALCAR level that synergistically activating the cAMP-PKA-CREB-BDNF pathway with significant neuromodulating actions.

In yet another aspect, the invention relates to synergistic bioactive compositions comprising combination of (3R)-3-acetyloxy-4-(trimethylazaniumyl) butanoate which is present in the range of 1-3000 mg and N-(4-Aminobutyl) guanidine which is present in the range of 1-1000 mg along with pharmaceutically acceptable excipients/carriers.

In one more aspect, the invention provides synergistic bioactive composition useful for treating neurological and psychiatric disorders like stress, depression, anxiety, obsessive compulsive disorder, bipolar disorder, unipolar disorder, conduct disorder, ADHD and like thereof.

In yet another aspect, the present invention provides a method of treating neurological and psychiatric disorders like stress, depression, anxiety, obsessive compulsive disorder, bipolar disorder, unipolar disorder, conduct disorder, ADHD and like thereof by administering effective amount of the composition of the present invention.

Abbreviations

ALCAR: acetyl-1-carnitine
mTOR: mechanistic target of rapamycin
cAMP: cyclic adenosine monophosphate
AMPA: α-amino-3-hydroxy-5-methyl-4-isoxazolepropionic acid
NAcc: Nucleus Accumbens
PFC: prefrontal cortex
MSNs: medium spiny neurons
NMDA: N-methyl-D-aspartate
BDNF: brain derived neurotrophic factor MDD: major depressive disorder
GAD: general anxiety disorders
CREB: cAMP response element-binding protein
PDE: phosphodiesterases
AC: Adenylyl cyclase
PKA: protein kinase A

BRIEF DESCRIPTION OF FIGURES AND DRAWINGS

The accompanying drawings illustrate some of the embodiments of the present invention and, together with the descriptions, serve to explain the invention. These drawings have been provided by way of illustration and not by way of limitation.

DETAILED DESCRIPTION OF THE INVENTION

Figure 1:
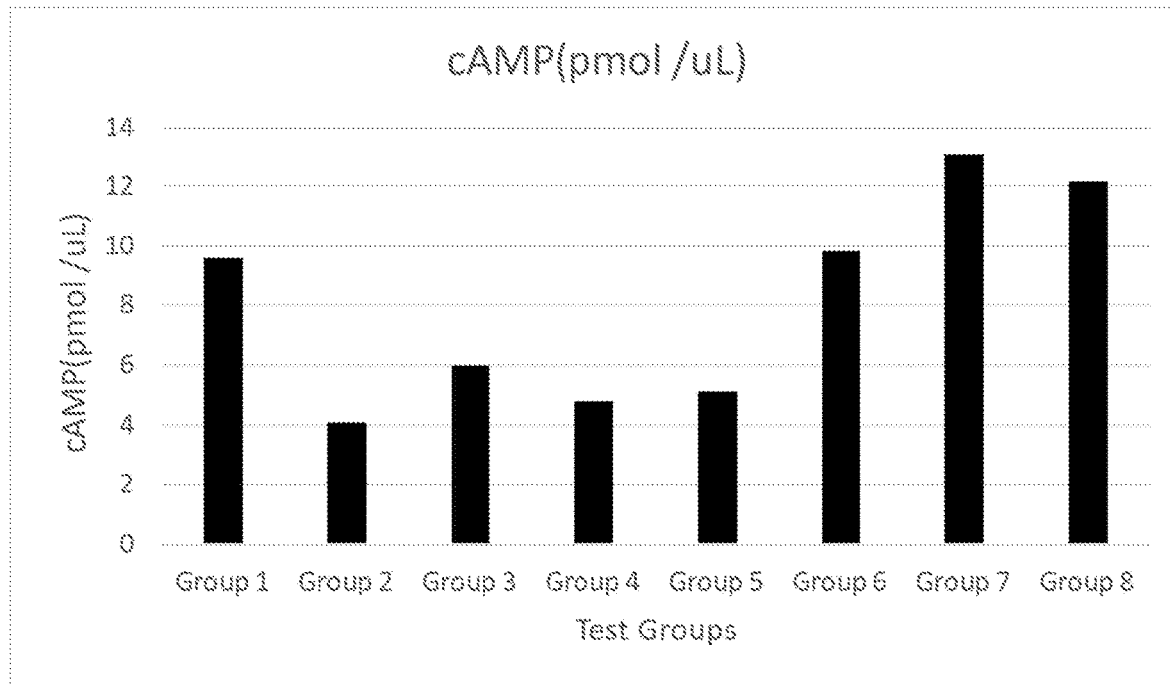
FIG. 1 illustrates CAMP level G1 (Cell Control), G2 (Positive Control), G3 (Reference standard), G4 (Test 1: (3R)-3-acetyloxy-4-(trimethylazaniumyl) butanoate), G5 (Test-2: N-(4-Aminobutyl) guanidine), G6 (Test-3: Low dose), G7 (Test-4: High dose), G8 (Test-5: Proposed dose)
Figure 2:
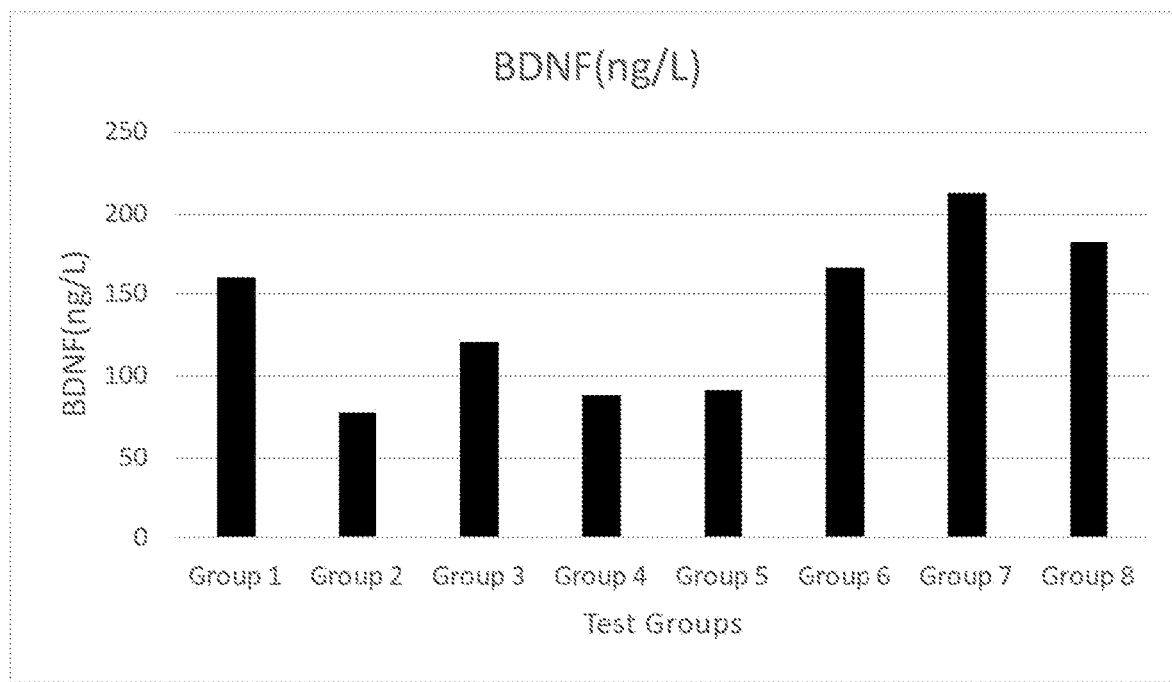
FIG. 2 illustrates BDNF level G1 (Cell Control), G2 (Positive Control), G3 (Reference standard), G4 (Test 1: (3R)-3-acetyloxy-4-(trimethylazaniumyl) butanoate), G5 (Test-2: N-(4-Aminobutyl) guanidine), G6 (Test-3: Low dose), G7 (Test-4: High dose), G8 (Test-5: Proposed dose)
Figure 3:
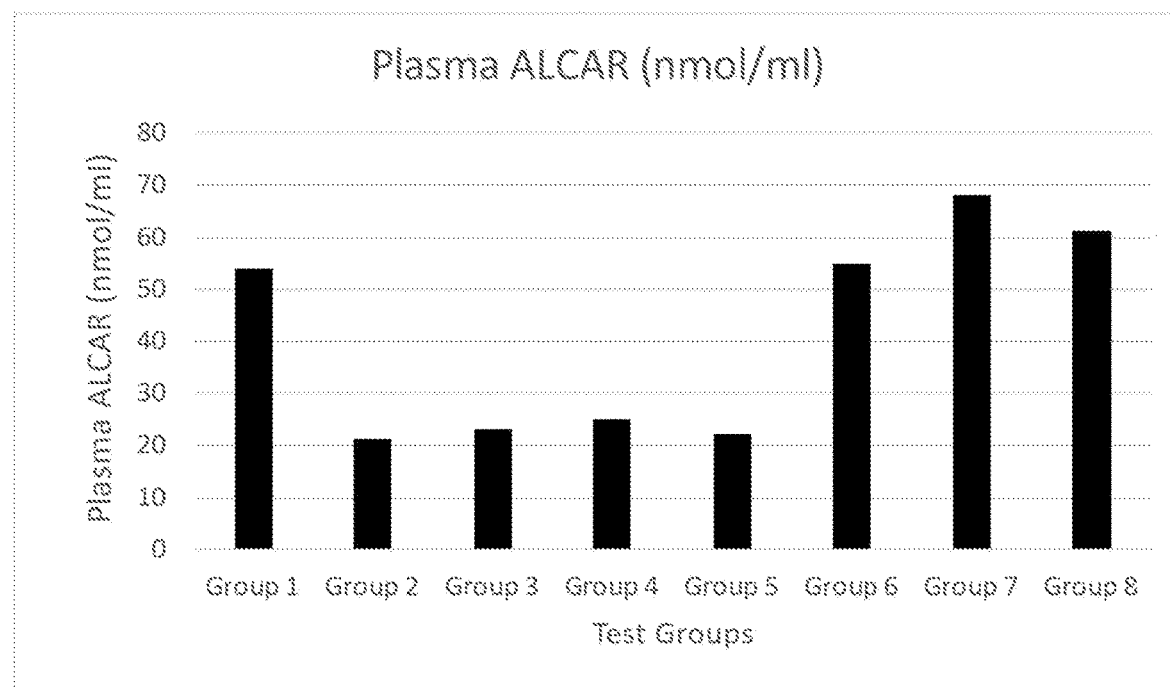
FIG. 3 illustrates Plasma ALCAR level G1 (Cell Control), G2 (Positive Control), G3 (Reference standard), G4 (Test 1: (3R)-3-acetyloxy-4-(trimethylazaniumyl) butanoate), G5 (Test-2: N-(4-Aminobutyl) guanidine), G6 (Test-3: Low dose), G7 (Test-4: High dose), G8 (Test-5: Proposed dose)
Figure 4:
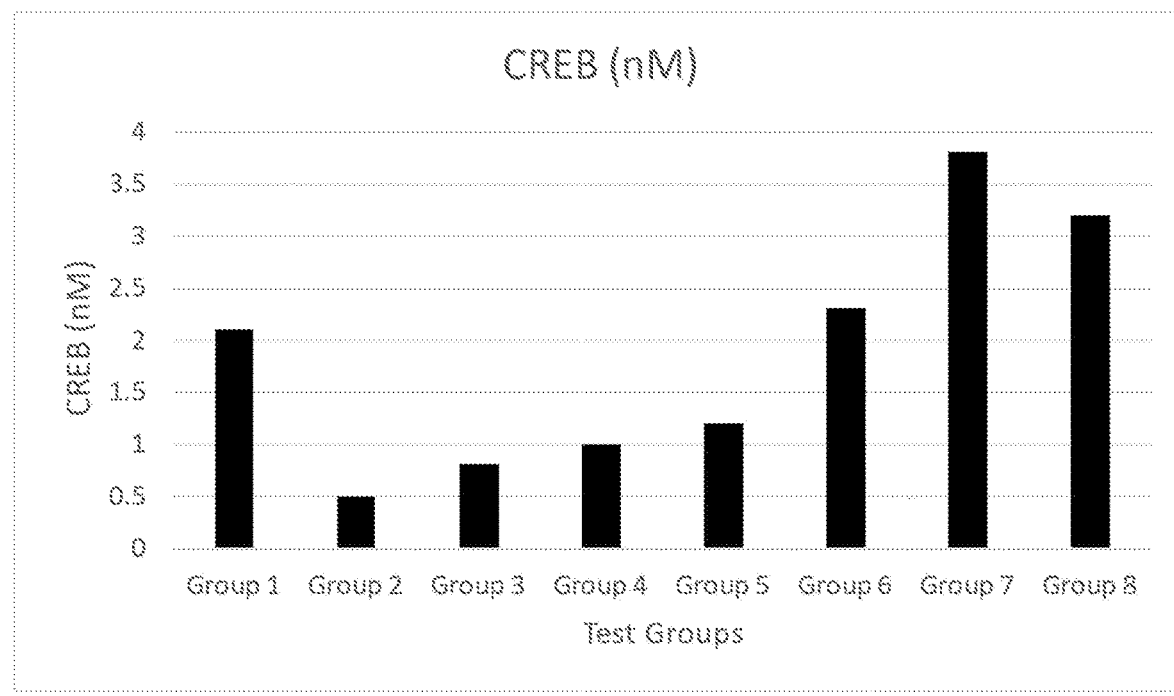
FIG. 4 illustrates CREB concentration G1 (Cell Control), G2 (Positive Control), G3 (Reference standard), G4 (Test 1: (3R)-3-acetyloxy-4-(trimethylazaniumyl) butanoate), G5 (Test-2: N-(4-Aminobutyl) guanidine), G6 (Test-3: Low dose), G7 (Test-4: High dose), G8 (Test-5: Proposed dose)
Figure 5:
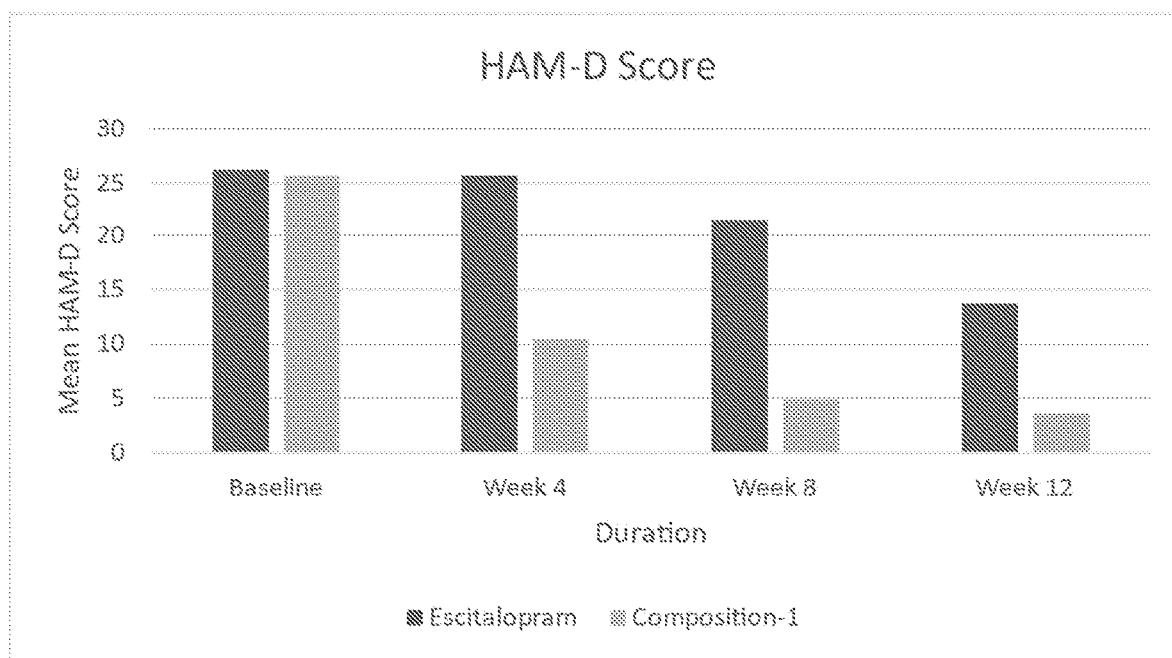
FIG. 5 illustrates HAM-D score of patients in treatment with Escitalopram and Composition 1 observed at time interval baseline, 4 weeks, 8 weeks and 12 weeks

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only and is not intended to be limiting in any manner or scope. Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a," "an," and "the" include plural reference unless the context clearly dictates otherwise. Also, the term 'composition' does not limit the scope of the invention for multiple compositions that can be illustrated for best mode of the invention.

The term "pharmaceutically/nutraceutically acceptable salt," as use herein, represents those salts which are within the scope of sound medical judgment, suitable for use in contact with the tissues of humans and animals without undue toxicity, irritation, allergic response and the like and are commensurate with a reasonable benefit/risk ratio.

Particularly the term "pharmaceutically-acceptable salts" refers to the relatively non-toxic, inorganic and organic acid addition salts of compounds, amino acid salt, sugar-based salt, alkali or alkaline earth metal salts, as well as solvates, co-crystals, polymorphs and the like of the salts. All modifications and substitutions that come within the meaning of the description and the range of their legal equivalents are to be embraced within their scope. A description using the transition "comprising" allows the inclusion of other elements to be within the scope of the invention.

In a preferred embodiment, the invention provides synergistic bioactive compositions comprising specific combination of (3R)-3-acetyloxy-4-(trimethylazaniumyl)butanoate and N-(4-aminobutyl)guanidine which are present in a specific weight ratio along with pharmaceutically acceptable excipients.

In another embodiment, the invention provides synergistic bioactive composition for ameliorating nucleus accumbens (NAcc) function via potentiating cAMP pathway.

In yet another embodiment, the present invention provides a synergistic bioactive composition for activating intracellular cyclic adenosine monophosphate (cAMP) secondary messenger pathway comprising therapeutically active exogenous combination of an effective amount of (3R)-3-acetyloxy-4-(trimethylazaniumyl)butanoate and N-(4-aminobutylaminobutyl)guanidine or salts thereof along with pharmaceutically acceptable excipients.

The present biologically active composition is composed of synergistic combination of (3R)-3-acetyloxy-4-(trimethylazaniumyl)butanoate and N-(4-Aminobutyl)guanidine which are present in therapeutically effective amount.

In preferred embodiment, the invention provides bioactive composition comprising combination of therapeutically effective amount of (3R)-3-acetyloxy-4-(trimethylazaniumyl)butanoate and N-(4-Aminobutyl)guanidine in a specific ratio, along with pharmaceutically acceptable excipients, wherein (3R)-3-acetyloxy-4-(trimethylazaniumyl) butanoate moiety promotes cAMP level, concomitantly N-(4-Aminobutyl)guanidine improves endogenous ALCAR level which synergistically activating the cAMP-PKA-CREB-BDNF pathway which enhance neuroplasticity and synaptogenesis in brain region.

(3R)-3-acetyloxy-4-(trimethylazaniumyl)butanoate is commonly known as Levocarnitine acetyl, O-Acetyl-L-carnitine. It is chemically known as spacer (3R)-3-acetoxy-4 (trimethylammonio)butanoate hydrochloride, (3R)-3-acetoxy-4-(trimethylammonio) butyrate, (3R)-3-acetyloxy-4-(trimethylazaniumyl)butanoate. It has molecular formula $CH_JNO_4$.

(3R)-3-acetyloxy-4-(trimethylazaniumyl)butanoate is an ester of the trimethylated amino acid L-carnitine. (3R)-3-acetyloxy-4-(trimethylazaniumyl)butanoate is more easily absorbed from the gut, and more readily crosses the blood-brain barrier. Further (3R)-3-acetyloxy-4-(trimethylazaniumyl)butanoate is stable and bioavailable molecule.

(3R)-3-acetyloxy-4-(trimethylazaniumyl)butanoate represents a major, natural supplement which promotes MFN2-induced mitochondrial fusion in the nucleus accumbens. (3R)-3-acetyloxy-4-(trimethylazaniumyl)butanoate can regulate mitochondria in neural circuits as well as Mitofusin 2 (MFN2) overexpression.

In another embodiment, the present invention provides the synergistic bioactive composition where (3R)-3-acetyloxy-4-(trimethylazaniumyl)butanoate facilitates beta oxidation and ATP production.

Acetyl-CoA is the primary substrate for the Krebs cycle, once it is de-acetylated, it is re-charged with an acetyl-group of (3R)-3-acetyloxy-4-(trimethylazaniumyl)butanoate for working of Krebs cycle and ATP production.

The adenylyl cyclase facilitates rate of conversion of adenosine triphosphate (ATP) to 3',5'-cyclic AMP (cAMP).

In another embodiment, the present invention provides synergistic bioactive composition comprising therapeutically effective amount of (3R)-3-acetyloxy-4-(trimethylazaniumyl) butanoate along with pharmaceutically acceptable salts thereof, wherein (3R)-3-acetyloxy-4-(trimethylazaniumyl) butanoate is present in the range of 1-3000 mg, preferably in the range of 1-1000 mg of total composition.

In another embodiment, the present invention provides the bioactive combination, wherein the synergistic effect is achieved by enhancing cAMP level in brain region and consequently improving synaptic formation and neuroplasticity.

In another embodiment, the invention provides synergistic bioactive compositions comprising N-(4-aminobutyl) guanidine and salts thereof, wherein the preferable salt is sulphate having molecular formula $C_5H_{16}N_4O_4S$.

In another preferred embodiment the N-4-Aminobutylguanidine salt is white crystalline N-4-Aminobutylguanidine sulphate. N-4-Aminobutylguanidine acts as a neuromodulator or co-transmitter which activates ALCAR that further up-regulates cAMP pathway which further leads to enhanced neuroplasticity and synaptogenesis in brain.

In another embodiment N-4-Aminobutylguanidine treatment effectively upregulates transcription factor CREB (cyclic adenosine monophosphate response element binding protein) that increase BDNF expression.

Further mTOR signalling plays a crucial role in the neuropathophysiology of depression. In another embodiment N-4-Aminobutylguanidine increases mTOR phosphorylation and BDNF levels in brain structures.

In yet another embodiment, the present invention provides synergistic bioactive composition comprising therapeutically effective amount of N-4-Aminobutylguanidine along with pharmaceutically acceptable salts thereof, wherein N-4-Aminobutylguanidine salt is present in the range of 1-1000 mg of total composition.

In another embodiment, the present synergistic composition where the synergistic combination of (3R)-3-acetyloxy-4-(trimethylazaniumyl) butanoate and N-4-Aminobutylguanidine provides antidepressant or anxiolytic effect associated with upregulation of mTOR and BDNF through ALCAR mediated cAMP activation in the brain.

In another embodiment, the present invention provides the bioactive combination elevates synthesis and intracellular levels of cAMP and CREB.

In another embodiment, the present invention provides synergistic bioactive composition, wherein the composition comprising therapeutically active exogenous blend of (3R)-3-acetyloxy-4-(trimethylazaniumyl) butanoate and N-4-Aminobutylguanidine salts thereof are present in suitable weight ratio, along with pharmaceutically acceptable excipients.

In yet another preferred embodiment, the invention provides synergistic bioactive composition stimulates G-protein-coupled receptors and, in turn, triggers cyclase adenosine monophosphate (cAMP) synthesis by adenylyl cyclase (AC) then, cAMP activates protein kinase A (PKA), which directly activates the molecular phosphorylation of transcription factors and further coordinates multiple signalling molecules transcription factors, such as cAMP response element-binding protein (CREB) and brain-derived neurotrophic factor (BDNF). BDNF is the target gene of CREB, which regulates the survival, maintenance and growth of neurons.

In another preferred embodiment, the present composition activates the cAMP-PKA-CREB-BDNF signalling pathway synergistically which relieve the symptoms related to cAMP depletion such as depression, anxiety, and cognitive function impairment.

In some embodiment, the invention provides the composition works synergistically in the brain specific region, where (3R)-3-acetyloxy-4-trimethylazaniumyl) butanoate and N-4-Aminobutylguanidine enhances mTOR signalling through the activation and functioning of ionotropic glutamate receptors, which improve neuroplasticity in NAcc and consequently normalize enlarged NAcc volume.

In some embodiment, the present invention provides the synergistic composition preserve BBB integrity and reduces the inflammation.

In one preferred embodiment the invention provides a synergistic bioactive composition for activating intracellular-cyclic adenosine monophosphate (cAMP) secondary messenger pathway comprising therapeutically active exogenous combination of an effective amount (3R)-3-acetyloxy-4-(trimethylazaniumyl) butanoate and N-4-aminobutylguanidine or salts thereof; wherein said bioactives are present in the weight ratio of 1:0.01 to 1:2; and pharmaceutically acceptable excipients.

In yet another preferred embodiment, the invention provides bioactive compositions for activating cAMP PKA-CREB-BDNF signalling pathway comprising exogenous blend of therapeutically active (3R)-3-acetyloxy-4-(trimethylazaniumyl) butanoate and N-4-aminobutylguanidine present in the weight ratio of 1:0.01 to 1:2, along with pharmaceutically acceptable excipients, wherein the theses two active ingredients act synergistically to activate cAMP.

In yet another preferred embodiment, the invention provides compositions for potentiating cAMP pathway comprising exogenous blend of therapeutically active (3R)-3-acetyloxy-4-(trimethylazaniumyl)butanoate and N-4-Aminobutylguanidine which are present in weight ratio of 1:0.01 to 1:2, along with pharmaceutically acceptable excipients, wherein the composition upregulates endogenous ALCAR that triggers nucleus transcription through cAMP-PKA-CREB-BDNF signalling pathway that substantially improves neuroplasticity and synaptogenesis.

In one more embodiment, the invention provides synergistic composition comprising (3R)-3-acetyloxy-4-(trimethylazaniumyl)butanoate present in a range of 25% to 99% by weight of the total composition.

In one more embodiment, the invention provides synergistic composition wherein the (3R)-3-acetyloxy-4-(trimethylazaniumyl)butanoate salt is white crystalline (3R)-3-acetyloxy-4-(trimethylazaniumyl)butanoate hydrochloride.

In another embodiment, the invention provides synergistic composition comprising white crystalline N-4-Aminobutylguanidine sulphate which is present in a range of 1% to 66% by weight of the total composition.

In another embodiment, the invention provides synergistic bioactive composition useful for enhancing cAMP level.

In another embodiment the invention provides the synergistic composition comprising therapeutically active exogenous combination of effective amount (3R)-3-acetyloxy-4-

(trimethylazaniumyl)butanoate and N-4-aminobutylguanidine which are present in the weight ratio of 1:0.01 to 1:2 along with pharmaceutically acceptable excipients, which improves the cAMP level by 3.1 to 4.0 folds over the positive control.

In another embodiment the invention provides the synergistic composition comprising therapeutically active exogenous combination of effective amount (3R)-3-acetyloxy-4-(trimethylazaniumyl)butanoate and N-4-aminobutylguanidine which are present in the weight ratio of 1:0.01 to 1:2 along with pharmaceutically acceptable excipients, which improves the BDNF level by 2.5 to 3.5 folds over the positive control.

In another embodiment the invention provides the synergistic composition comprising therapeutically active exogenous combination of effective amount (3R)-3-acetyloxy-4-(trimethylazaniumyl) butanoate and N-4-Aminobutylguanidine which are present in the weight ratio of 1:0.01 to 1:2 along with pharmaceutically acceptable excipients, which improves the plasma ALCAR level by 3.1 to 4.0 folds over the positive control.

In another embodiment the invention provides the synergistic composition comprising therapeutically active exogenous combination of effective amount (3R)-3-acetyloxy-4-(trimethylazaniumyl) butanoate and N-4-aminobutylguanidine which are present in the weight ratio of 1:0.01 to 1:2 along with pharmaceutically acceptable excipients, which improves the CREB level by 7.2 to 8.5 folds over the positive control.

In yet another embodiment the invention provides the synergistic composition comprising therapeutically active exogenous combination of effective amount (3R)-3-acetyloxy-4-(trimethylazaniumyl) butanoate and N-4-aminobutylguanidine which are present in the weight ratio of 1:0.01 to 1:2 along with pharmaceutically acceptable excipients, which lowers the HAM-D score by 3.1 to 3.9 over the baseline.

In another embodiment the invention provides the synergistic composition comprising therapeutically active exogenous combination of effective amount (3R)-3-acetyloxy-4-(trimethylazaniumyl)butanoate and N-4-aminobutylguanidine which are present in the weight ratio of 1:0.01 to 1:2 along with pharmaceutically acceptable excipients, composition as claimed in claim 1, wherein the responder remission rate in female is 100% over baseline.

In yet another embodiment the invention provides the synergistic bioactive composition for treating disease conditions or disorders related to depletion of secondary messenger pathway.

In another embodiment the invention provides bioactive composition wherein the composition is orally administered with effective unit dose of 10 mg to 1000 mg.

In some embodiment, the present invention provides synergistic bioactive composition for brain specific region comprising specific combination of (3R)-3-acetyloxy-4-(trimethylazaniumyl)butanoate and N-4-aminobutylguanidine; wherein (3R)-3-acetyloxy-4-(trimethylazaniumyl)butanoate promotes MFN2-induced mitochondrial fusion in the nucleus accumbens, concomitantly N-4-aminobutylguanidine enhances mTOR signalling, which enhance neuroplasticity in NAcc and consequently normalize enlarged NAcc volume.

In another preferred embodiment, the present invention provides synergistic composition for treating depressive symptoms in female population, wherein the composition reduces BBB leakiness by restoring the estrogen level. The restored estrogen upregulates tight junction protein claudin-5 thus reduces inflammation and subsequently attenuates depression.

In yet another embodiment the present invention provides the synergistic composition which regulates epigenetic changes observed in depressive subjects. Moreover, the composition synergistically enhances ALCAR levels that induces rapid and long-lasting antidepressant effect via epigenetic mechanism of histone acetylation.

In yet another aspect, the present invention provides a method of treating neurological and psychiatric disorders like stress, depression, anxiety, obsessive compulsive disorder, bipolar disorder, unipolar disorder, conduct disorder, ADHD and like thereof by administering effective amount of the composition of the present invention.

Histone acetylation helps to regulate expression of key genes involved in synaptic plasticity, regulation of BDNF secretion and synaptic glutamate release Further the present composition ameliorates glutamatergic dysfunction and neuronal atrophy in mood regulatory brain regions such as hippocampus and amygdala.

Since cyclic AMP is a second messenger and plays vital role in cell signalling, it has been implicated in various disorders but not restricted to the roles such as deregulation of cAMP pathways and an aberrant activation of cAMP-controlled genes is linked to the growth of some cancers, prefrontal cortex disorders neurogenic inflammation and causing migraine, ADHD, infectious disease, depression, anxiety, stress, bipolar disorder, obsessive-compulsive disorder (OCD), or conduct disorder (CD), unipolar disorder, cognitive dysfunction.

In another embodiment, the invention provides composition which is useful in the treatment of treatment-resistant or treatment-refractory depression, early onset, female depression like perimenopausal, depression postpartum, depression postmenopausal and childhood adversity. Children with a family history of violence, alcohol abuse, or physical or sexual abuse are at greater risk for suicide. Those are with symptoms of childhood depression.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum cAMP level), and/or minimize at least one clinical symptom related such as anxiety, stress, OCD, and MDD.

In another embodiment, the present invention provides synergistic bioactive composition which is useful in treatment of the commonest and most severe psychiatric disorders, such as depression, schizophrenia, obsessive-compulsive disorder, and other anxiety disorders, as well as in addiction, including drugs abuse, alcoholism and smoking, other psychiatric disorders such as bipolar disorder, attention deficit/hyperactivity disorder and post-traumatic stress disorder. Neuromodulation interventions targeting the nucleus accumbens are nowadays applied in selected patients suffering from treatment-resistant depression, Tourette syndrome and addiction to drugs or alcohol, ageing, immune system disorders and inflammatory diseases.

In another embodiment, the invention provides synergistic bioactive composition for activating cAMP signalling particularly in depression, wherein the depression is selected from the group consisting of: unipolar depression, bipolar depression, spirituality depression, reactive depression, secondary depression, seasonal depression, postpartum depression and menopausal depression.

The term 'subject in need thereof' pertains to subject preferably mammal, more preferably human suffering or suspected with cAMP depletion.

In the context of the present invention, the term "treatment" relates to alleviate, mitigate, prophylaxis, attenuate, manage, regulate, modulate, control, minimize, lessen, decrease, down modulate, up regulate, moderate, inhibit, reverse, restore, suppress, reverse, limit, block, decrease, prevent, inhibit, stabilize, ameliorate or cure, heal mental disorder, psychiatry, agitation, anxiety, depression, mania, paranoia, psychosis, cognitive impairment, social problems, suicide, anxiety disorders, dysthymia.

Notably, the present synergistic composition is non-hazardous, non-toxic, and safe for human consumption without any adverse effects, therefore the present bioactive composition can also be used under preventive therapy/adjuvant therapy add-on therapy/combination/adjunctive therapy in a subject in need thereof.

Certain compounds of the present invention can exist in unsolvated forms as well as solvated forms, including hydrated forms. Further some compounds of the present invention can exist in multiple crystalline or amorphous forms ("polymorphs"). Compounds of the invention can also exist in geometric or enantiomeric or stereoisomeric forms.

As used herein, the term "pharmaceutically acceptable carriers, diluents or excipients" is purported to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethylene glycol matrix which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic compositions, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal, or oral.

In some embodiment, the present synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. Further, the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), sachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a bolus, electuary or paste, bioactive bar, energy bars (candy bars), powder, energy drink, ready to drink, granule sachet.

Further, the present composition can be formulated in the form of age-appropriate pediatric oral dosage forms such as syrup, minitablets, chewable formulations, orodispersible films, orodispersible tablets and bioadhesive buccal tablets. It can also be prepared in the form of snack, chocolate bars or other confectionery food products.

In another embodiment, the synergistic composition of the present invention is non-toxic, cost effective, enriched with bioactive ingredients, and provides safeguard against problems associated with cAMP deficiency without any adverse effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, O-cyclodextrin, methylated-f-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminium silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1 to 40% by weight of the composition/formulation.

In some embodiment, the antioxidant is selected from tocopherol (vitamin E), sesamol, guaiac resin, methionine, beta-carotene, lycopene, lutein, zeaxanthin, butylated hydroxy anisole (BHA), butylated hydroxytoluene (BHT), sodium ascorbate, sodium metabisulfite (SMB), I-carnosine, propyl gallate (PG), tertiary butyl hydroquinone, cysteine (CYS), citric acid, tartaric acid, phosphoric acid and ascorbic acid.

In some embodiment of the invention, the amount of antioxidant in the composition/formulation is present in the range of 0.1 to 10% by wt. of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 10.0% by weight of the total composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, acetylated monoglycerides, castor oil, mineral oil and like thereof.

In some embodiments of the invention, the plasticizer in the composition/formulation is present in a range of 0.1% to 5.0% by weight of the total composition/formulation.

In some embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1 to 20% w/w of unit dose.

In yet another embodiment, the invention provides the synergistic composition comprising a therapeutic blend of (3R)-3-acetyloxy-4-(trimethylazaniumyl) butanoate and N-4-Aminobutylguanidine along with pharmaceutical excipients, wherein the pharmaceutical excipients are selected from a diluent, a binder, a lubricant, a glidant, an additive, a surfactant, a stabilizer or mixtures thereof.

In a preferred embodiment, the invention provides the composition wherein the pharmaceutically acceptable excipients are selected from a group consisting of the diluent which is present in a range of 1 to 30%; the binder which is present in a range of 0.5 to 25%; the lubricant which is present in a range of 0.1 to 10.0%; the glidant which is present in a range of 0.1 to 5.0%; the additive which is present in a range of 0.1 to 10%; the surfactant which is present in a range of 0.1 to 5.0%; the stabilizer which is present in a range of 0.1 to 5.0%; %; the antioxidant which is present in a range of 0.1 to 5.0%; and the plasticizer which is present in a range of 0.1 to 5.0%; by weight of total composition.

In further embodiment compositions containing compounds of the invention, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 2500 mg per day, preferably about 10 mg per day to about 1000 mg per day.

In certain embodiments, the invention provides the potent composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention, and does not pose a limitation on the scope of the invention unless otherwise claimed.

Various other examples of compositions and modifications or adaptations thereof can be devised by a person skilled in the art after reading the foregoing preferred embodiments without departing from the spirit and scope of the invention. All such further examples, modifications and adaptations are included within the scope of the invention.

It will be appreciated by those versed in the art that the present invention makes available novel and useful nutraceutical compositions and nutraceutical acceptable salts thereof, which have neuroprotective effects in several administration forms. Also, it will be understood by those with knowledge in the dietary supplement and nutraceutical art, that many embodiments of this invention may be made without departing from the spirit and scope of the invention, and the invention is not to be construed as limited, as it embraces all equivalents therein.

The invention may be further illustrated by the following examples, which are for illustrative purposes only and should not be construed as limiting the scope of the invention in anyway.

The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Having described the basic aspects of the present invention, the following non-limiting examples illustrate specific embodiments thereof. Those skilled in the art will appreciate that many modifications may be made in the invention without changing the essence of invention.

Example—1

Compounds (3R)-3-acetyloxy-4-(trimethylazaniumyl)butanoate, N-4-aminobutylguanidine and salts thereof have been obtained commercially.

i. Composition 1: Synergistic Blend

| Ingredient | w/w % |
|---|---|
| (3R)-3-acetyloxy-4-(trimethylazaniumyl)butanoate | 25% to 99% |
| N-4-aminobutylguanidine Sulphate | 1% to 66% | ii. Composition 2: Tablet/Capsule

| Ingredient | w/w % unit dose |
|---|---|
| (3R)-3-acetyloxy-4-(trimethylazaniumyl)butanoate | 25 to 99% |
| N-4-aminobutylguanidine Sulphate | 1 to 66% |
| Excipient | 5-20% |
| Average Weight | 100% | iii. Composition 3: Tablet/Capsule

| Ingredient | w/w % unit dose |
|---|---|
| (3R)-3-acetyloxy-4-(trimethylazaniumyl)butanoate | 45-99% |
| N-4-aminobutylguanidine Sulphate | 1-50% |
| Diluents | 1-10% |
| Binders | 0.1-8% |
| Glidants | 0.1-5% |
| Lubricants | 0.1-5% |
| Stabilizers | 0.1-5% |
| Additives | 1-10% |
| Antioxidant | 0.01-5% |
| Solvents | QS | iv. Composition 4: Tablet/Capsule

| Ingredient | mg per unit dose |
|---|---|
| (3R)-3-acetyloxy-4-(trimethylazaniumyl)butanoate | 500 |
| N-4-aminobutylguanidine Sulphate | 250 |
| Magnesium Stearate | 1-10 |
| Hydroxypropyl Methylcellulose | 1-10 |
| Microcrystalline Cellulose | 1-20 |
| PVP K-30 | 5-10 |
| Silicon dioxide | 1-10 |
| Talc | 1-10 |
| Mannitol | 1-20 |
| Propylene Glycol | QS |
| Water | QS |
| Average weight | 760-800 mg | v. Composition 5: Tablet/Capsule

| Ingredient | mg per unit dose |
|---|---|
| (3R)-3-acetyloxy-4-(trimethylazaniumyl)butanoate | 500 |
| N-4-aminobutylguanidine Sulphate | 5 |
| Sodium Benzoate | 1-10 | vi. Composition 6: Tablet/Capsule (continued)

| Ingredient | mg per unit dose |
| --- | --- |
| Magnesium Stearate | 1-20 |
| Ascorbic acid | 2-10 |
| Microcrystalline Cellulose | 2-20 |
| Colloidal Silicon dioxide | 5-15 |
| Hydroxypropyl Methylcellulose | 2-10 |
| triethyl citrate | 2-10 |
| PVPP | 5-10 |
| Talc | 1-10 |
| Tween 80 | 1-10 |
| Mannitol | 5-20 |
| Alcohol | QS |
| Water | QS |
| Average weight | 510-570 mg | vi. Composition 6: Tablet/Capsule

| Ingredient | mg per unit dose |
| --- | --- |
| (3R)-3-acetyloxy-4-(trimethylazaniumyl)butanoate | 500 |
| N-4-aminobutylguanidine Sulphate | 500 |
| Butylated hydroxytoluene | 1-5 |
| Microcrystalline Cellulose | 2-20 |
| Silicon dioxide | 1-10 |
| Hydroxypropyl Methylcellulose | 2-10 |
| Stearic acid | 2-10 |
| Dibasic calcium phosphate | 1-20 |
| Pregelatinized starch | 5-10 |
| Talc | 1-10 |
| Tween 80 | 1-10 |
| Polydextrose | 1-10 |
| PEG | QS |
| Water | QS |
| Average weight | 1010-1100 mg | vii. Composition 7: Tablet/Capsule

| Ingredient | mg per unit dose |
| --- | --- |
| (3R)-3-acetyloxy-4-(trimethylazaniumyl)butanoate | 250 |
| N-4-aminobutylguanidine Sulphate | 250 |
| Microcrystalline Cellulose | 1-10 |
| Silicon dioxide | 1-10 |
| Butylated hydroxytoluene | 1-5 |
| Glycerin | 1-10 |
| Ethyl Cellulose | 1-10 |
| Hydroxypropyl Methylcellulose | 1-10 |
| Magnesium Stearate | 2-10 |
| Polyvinylpolypyrrolidone | 1-10 |
| Talc | 1-10 |
| Polysorbate 20 | 1-10 |
| Mannitol | 1-10 |
| IPA | QS |
| Water | QS |
| Average weight | 510-550 mg | viii. Composition 8: Tablet/Capsule

| Ingredient | mg per unit dose |
| --- | --- |
| (3R)-3-acetyloxy-4-(trimethylazaniumyl)butanoate | 100 |
| N-4-aminobutylguanidine Sulphate | 200 |
| Silicon Dioxide | 1-10 |
| Medium-chain triglycerides | 1-5 |
| Microcrystalline Cellulose | 2-20 |
| Dibasic Calcium Phosphate | 2-20 |
| Magnesium Stearate | 2-10 |
| Croscarmellose sodium | 2-10 |
| Polyvinylpyrrolidone | 1-20 |
| Talc | 1-10 |
| Corn Starch | 1-10 |
| Sodium ascorbate | 1-10 |
| Propylene glycol | 1-10 |
| Water | QS |
| Average weight | 310-380 mg | ix. Composition 9: Tablet/Capsule

| Ingredient | mg per unit dose |
| --- | --- |
| (3R)-3-acetyloxy-4-(trimethylazaniumyl)butanoate | 100 |
| N-4-aminobutylguanidine Sulphate | 100 |
| Microcrystalline Cellulose | 1-10 |
| Colloidal silicon dioxide | 1-10 |
| Hydroxypropyl Methylcellulose | 1-10 |
| Magnesium Stearate | 2-10 |
| Polyvinylpyrrolidone | 1-10 |
| Calcium Phosphate | 1-10 |
| Ascorbic Acid | 1-10 |
| Polysorbate 20 | 1-10 |
| Talc | 1-5 |
| Sucrose | 1-10 |
| Mannitol | 1-10 |
| Glycerol | 1-10 |
| Average weight | 220-250 mg | x. Composition 10: Tablet/Capsule

| Ingredient | mg per unit dose |
| --- | --- |
| (3R)-3-acetyloxy-4-(trimethylazaniumyl)butanoate | 250 |
| N-4-aminobutylguanidine Sulphate | 50 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 310-350 mg | xi. Composition 11: Tablet/Capsule

| Ingredient | mg per unit dose |
| --- | --- |
| (3R)-3-acetyloxy-4-(trimethylazaniumyl)butanoate | 250 |
| N-4-aminobutylguanidine Sulphate | 100 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |

-continued

| Ingredient | mg per unit dose |
|---|---|
| Polyvinylpyrrolidone | 1-10 |
| Mineral Oil | 1-10 |
| Sodium benzoate | 1-10 |
| Citric Acid | 1-10 |
| Polysorbate 80 | 1-10 |
| Talc | 1-5 |
| Sucrose | 1-10 |
| Mannitol | 1-10 |
| Water | QS |
| Average weight | 360-400 mg | xii. Composition 12: Tablet/Capsule

| Ingredient | mg per unit dose |
|---|---|
| (3R)-3-acetyloxy-4-(trimethylazaniumyl)butanoate | 500 |
| N-4-aminobutylguanidine Sulphate | 50 |
| Microcrystalline Cellulose | 1-10 |
| Colloidal Silicon dioxide | 1-10 |
| Hydroxypropyl cellulose | 1-10 |
| Magnesium Stearate | 2-10 |
| Calcium Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 560-620 mg | xiii. Composition 13: Tablet/Capsule

| Ingredient | mg per unit dose |
|---|---|
| (3R)-3-acetyloxy-4-(trimethylazaniumyl)butanoate hydrochloride | 500 |
| N-4-aminobutylguanidine Sulphate | 250 |
| Magnesium Stearate | 1-10 |
| Hydroxypropyl Methylcellulose | 1-10 |
| Microcrystalline Cellulose | 1-20 |
| PVP K-30 | 5-10 |
| Silicon dioxide | 1-10 |
| Talc | 1-10 |
| Mannitol | 1-20 |
| Propylene Glycol | QS |
| Water | QS |
| Average weight | 760-800 mg |

Example 2: Animal Study

1. Biochemical Parameter:

To assess the effectiveness of test substance on modulation of cAMP and evaluation of BDNF in Rat Glioblastoma cells.

Procedure a. Outline of the Method:

The cytotoxicity profiling of the test substance was carried out to find the safe dose on C6 cells. The dose exhibiting cell viability above 85% was selected for the cAMP assay. The levels of cAMP in the cell lysate were measured using a suitable ELISA kit to infer the modulatory effect.

10 mg of test substance was separately dissolved in 100 μL of DMSO and volume was made up with Ham's F-12 medium supplemented with 2% inactivated FBS to obtain a stock solution of 10 mg/mL concentration and sterilized by 0.22μ syringe filtration. Serial two-fold dilutions were prepared from this stock solution for further studies. Similarly, the toxicity inducer (Clozapine) and inhibitor (Escitalopram) was weighed and diluted to make a stock solution to perform the cytotoxicity profiling.

b. Cell Line and Culture Medium:

C6 (Rat Glioblastoma) cell line was procured from NCCS, India. Stock cells was cultured in Ham's F-12 medium supplemented with 10% inactivated Fetal Bovine Serum (FBS), penicillin (100 IU/ml), streptomycin (100 μg/ml) and amphotericin B (5 μg/ml) in a humidified atmosphere of 5% $CO_2$ at 37° C. until confluent. Passaging was done by centrifuging the cells, followed by seeding the pellet into a tissue culture vessel. The stock cultures were grown in 25 $cm^2$ culture flasks and all experiments will be carried out in 96 microtitre plates (Tarsons India Pvt. Ltd., Kolkata, India).

c. Determination of cell Viability by MTT Assay:

The monolayer cells were counted and adjusted to 1.0× $10^5$ cells/ml) using Ham's F-12 containing 10% FBS. To each of the wells, of the 96 well plate, 0.1 mL of the diluted cell suspension (approximately one lakh cells per well) was added. After 24 h, when a partial monolayer was formed, the supernatant will be flicked off, wash the monolayer once with medium and add different concentrations of test substance (1000-31.25 μg/mL) to the partial monolayer in microtitre plate. The plates were gently shake and incubated for 3 h at 37'C in 5% $CO_2$ atmosphere. The supernatant was removed and propanol will be added to solubilize the formazan. The absorbance was measure using a microplate reader at a wavelength of 540 nm. The percentage growth inhibition was calculated using the standard formula.

TABLE 1

Group design

| Group | Group Description | Dose | Expected Outcome |
|---|---|---|---|
| 1 | Cell control (Negative) | Maintenance medium | Basal level |
| 2 | Positive control | Clozapine-25 mg | Decreased levels of cAMP and BDNF |
| 3 | Reference standard | Escitalopram-10 mg | Increased levels of cAMP and BDNF |

TABLE 1-continued

Group design

| Group | Group Description | Dose | Expected Outcome |
|---|---|---|---|
| 4 | Test-I | (3R)-3-acetyloxy-4-(trimethylazaniumyl)butanoate-Proposed dose-500 mg | Increased levels of cAMP and BDNF |
| 5 | Test-II | N-4-aminobutylguanidine-Proposed dose 250 mg | Increased levels of cAMP and BDNF |
| 6 | Test-III | (3R)-3-acetyloxy-4-(trimethylazaniumyl)butanoate + N-4-aminobutylguanidine-Low dose 500 mg: 5 mg | Increased levels of cAMP and BDNF |
| 7 | Test-IV | (3R)-3-acetyloxy-4-(trimethylazaniumyl)butanoate + N-4-aminobutylguanidine-High dose 500 mg: 500 mg | Increased levels of cAMP and BDNF |
| 8 | Test-V | (3R)-3-acetyloxy-4-(trimethylazaniumyl)butanoate + N-4-aminobutylguanidine-Proposed dose 500 mg: 250 mg | Increased levels of cAMP and BDNF | d. Estimation of Modulatory Effect of Test Substance on cAMP Levels in C6 cells:

To perform the assay, cells were seeded in 24-well plates containing 500 NL complete Ham's F-12 with 4.5 g/L glucose. After 24 h, the confluent monolayer of cells was firstly incubated with the corresponding inhibitor (Escitalopram) compound for 1-4 h (based on standardization) minutes in the incubator at 37'C and 5% $CO_2$. Then, the selected dose of test substances and positive control (Clozapine) was added to the cells. After 28 hours of incubation, the cell supernatants from respective treatment wells were collected and assayed to estimate the levels of cyclic AMP using a commercially available kit.

e. Estimation of BDNF Levels in C6 Cells:

To perform the assay, cells were seeded in 24-well plates containing 500 μL complete Ham's F-12 with 4.5 g/L glucose. After 24 h, the confluent monolayer of cells was firstly incubated with the corresponding inhibitor compound for 1-4 h (based on standardization) minutes in the incubator at 37° C. and 5% $CO_2$. Then, the selected dose of test substances and positive control was added to the cells. After 28 hours of incubation, the cell supernatants from respective treatment wells were collected and assayed to estimate the levels of BDNF using a commercially available Rat BDNF ELISA kit.

f. Estimation of ALCAR Plasma Level (Nmol/Ml): Assay Performed by ALCAR ELISA Kit g. Estimation of CREB (Cyclic AMP Response Element-Binding Protein) nM Results:

TABLE 2

| Treatment Groups | cAMP (pmol/μL) | BDNF (ng/L) | Plasma ALCAR (nmol/ml) | CREB (nM) |
|---|---|---|---|---|
| Group 1 | 9.6 | 160 | 54 | 2.1 |
| Group 2 | 4.1 | 77 | 21 | 0.5 |
| Group 3 | 6.0 | 121 | 23 | 0.8 |
| Group 4 | 4.8 | 88 | 25 | 1.0 |
| Group 5 | 5.1 | 91 | 22 | 1.2 |
| Group 6 | 9.8 | 166 | 55 | 2.3 |
| Group 7 | 13.1 | 212 | 68 | 3.8 |
| Group 8 | 12.2 | 182 | 61 | 3.2 |

Discussion and Conclusion

The estimation of modulatory effect of test substance on biochemical parameters were analysed in C6 (Rat Glioblastoma) cell. The combination of (3R)-3-acetyloxy-4-(trimethylazaniumyl) butanoate and N-4-Aminobutylguanidine in low, high and proposed dose i.e. G6, G7 and G8 shown significant increase in secondary messenger i.e. cAMP and synaptic protein i.e. BDNF. This indicated the increase in synapse number and neuroplasticity.

Further, the plasma ALCAR level and CREB concentration significantly was increased in low, high and proposed dose as compared to reference drug.

2. Behavioural Parameters:

Evaluation of physical parameters of the test substances in experimental rat.

Animal House Conditions

Lighting: 12/12 hour light-dark cycle
Temperature: 22±3° C.
Relative Humidity: 30 to 70%
Animals had continuous access to fresh, potable, uncontaminated drinking water.
Feed: Normal chow diet
Each animal was marked by picric acid and numbering was given individually to each animal.
Each cage was numbered separately to identify the group. In each cage single animal was housed in standard stainless-steel cage having facilities for pelleted food and drinking water in bottle.

Test System and Animal Husbandry:
Species: Rat
Strain: Wister
Sex: Male
No. of animals: 48 Animals (n=6 per group)
Body weight: 180-200 gm Group, Designation and Dose Levels:

TABLE 3

Animal grouping and treatment details
Vehicle details: 0.5% of Carboxy Methyl Cellulose sodium was used as a vehicle for test formulation

| Groups | Group Description | Human Dose | No. of animals |
|---|---|---|---|
| Group 1 | Normal control (Cell control) | Vehicle | 6 |
| Group 2 | Disease Control | Clozapine-25 mg | 6 |
| Group 3 | Reference standard | Escitalopram-10 mg | 6 |
| Group 4 | Test 1-(3R)-3-acetyloxy-4-(trimethylazaniumyl)butanoate | 500 mg | 6 |
| Group 5 | Test 2-N-4-aminobutylguanidine | 250 mg | 6 |
| Group 6 | Test 3: (3R)-3-acetyloxy-4-(trimethylazaniumyl)butanoate + N-4-aminobutylguanidine [Low dose] | [500 mg + 5 mg] | 6 |
| Group 7 | Test 4: (3R)-3-acetyloxy-4-(trimethylazaniumyl)butanoate + N-4-aminobutylguanidine [High dose] | [500 mg + 500 mg] | 6 |
| Group 8 | Test 5: (3R)-3-acetyloxy-4-(trimethylazaniumyl)butanoate + N-4-aminobutylguanidine [Proposed dose] | [500 mg + 250 mg] | 6 |

Administration and Procedure—

All the animals were acclimatized for at least 5 days under controlled environmental condition.

Total 48 animals were divided into seven groups consisting of 6 animals per group.

Normal control (G1) group receiving vehicle, disease control (G2) group receiving Clozapine, Standard group (G3) receiving Escitalopram and treatment groups (G4, G5, G6, G7 and G8) were treated with the test substances.

The tests were performed by the known technique.

The following behavioural test were conducted at the end of the treatment,

Force Swim Test

Open Field Test

Behavioural at Novel Object Test

Behaviour at Elevated Plus Maze (EPM) test

Results

TABLE 4

Force Swim Test and Open Filed Test

| Treatment groups | Force Swim Test Immobility (Seconds) | Open Field Test Latency to reach center (Sec) | Open Field Test Distance walked in corners (cm) |
|---|---|---|---|
| Group 1 | 53 | 18 | 1600 |
| Group 2 | 189 | 38 | 2200 |
| Group 3 | 68 | 26 | 1900 |
| Group 4 | 55 | 27 | 1860 |
| Group 5 | 59 | 25 | 1820 |
| Group 6 | 52 | 19 | 1700 |
| Group 7 | 31 | 14 | 1480 |
| Group 8 | 43 | 16 | 1620 |

TABLE 5

Behavioural at Novel Object Test

| Treatment groups | Latency to reach Novel Object (sec) | Time Spent sniffing the object (%) | Number of times sniffing the object (times) |
|---|---|---|---|
| Group 1 | 48 | 04 | 36 |
| Group 2 | 03 | 13 | 62 |
| Group 3 | 32 | 09 | 48 |
| Group 4 | 35 | 08 | 49 |
| Group 5 | 36 | 09 | 47 |
| Group 6 | 42 | 06 | 41 |
| Group 7 | 56 | 03 | 29 |
| Group 8 | 49 | 04 | 35 |

TABLE 6

Behavior at Elevated Plus Maze (EPM) test

| Treatment groups | Time in the open arms (%) | Number of entries in to open arm (times) | time spent head dipping (%) | Number of times head dipping (times) | Time Spent Rearing (%) | Number of times rearing (times) |
|---|---|---|---|---|---|---|
| Group 1 | 06 | 04 | 05 | 07 | 09 | 12 |
| Group 2 | 15 | 10 | 21 | 18 | 19 | 25 |
| Group 3 | 11 | 07 | 12 | 12 | 16 | 18 |
| Group 4 | 12 | 08 | 11 | 12 | 15 | 18 |
| Group 5 | 11 | 07 | 10 | 11 | 13 | 16 |
| Group 6 | 08 | 06 | 07 | 08 | 09 | 11 |
| Group 7 | 05 | 03 | 02 | 04 | 03 | 06 |
| Group 8 | 06 | 04 | 04 | 05 | 05 | 08 |

Discussion

The present investigation demonstrated anxiety-related behaviour in rodent models of CNS disorders.

Table 4 represents the force swim and open field test where the Immobility and latency time observed in the G6, G7 and G8 treated groups is comparatively lower over the positive control.

Table 5 represent behavioural at novel object test where latency time spent towards the novel objects indicated better memory and learning ability. This test is based on the spontaneous tendency of rats to spend more time exploring a novel object than a familiar one.

Table 6 related to Elevated Plus Maze (EPM) test where time spent in the arms is less over the positive control.

Conclusion

The results showed that the combination of (3R)-3-acetyloxy-4-(trimethylazaniumyl)butanoate and N-4-Aminobutylguanidine at different ratio or dose works better in the treatment of anxiety, depression as compared to traditional antidepressants.

Example 3—Clinical Study

A Double-blind, Fixed-dose Study of Composition-1 vs Escitalopram in Adult Patients with Major Depressive Disorder Composition-1—(3R)-3-acetyloxy-4-(trimethylazaniumyl)butanoate+N-4-Aminobutylguanidine—500 mg+250 mg Reference—Escitalopram—20 mg Study Design and Participants:

A double-blind, Fixed-dose study, 80 participants (males and females) with major depression were randomly assigned to receive test samples. Age eligibility for study include 18 Years to 65 Years (Adult, Older Adult)

Participants were evaluated at visits at screening, baseline/randomization, and 4, 8, and 12 weeks after randomization. Masking—Triple (Participant, Investigator, Outcomes Assessor); Parallel Assignment Inclusion Criteria Patients must meet Diagnostic and Statistical Manual, Fourth Edition, Text Revision (DSM-IV-TR) diagnostic criteria for Major Depressive Disorder.

The patient's current depressive episode must be at least 8 weeks in duration.

Exclusion Criteria

Women who are pregnant, women who will be breastfeeding during the study, and women with childbearing potential who are not practicing a reliable method of birth control.

Patients with a history of meeting DSM-IV-TR criteria for: a. any manic or hypomanic episode; b, schizophrenia or any other psychotic disorder; c. obsessive-compulsive disorder.

Patients Who are Considered a Suicide Risk

Patients with a history of seizures (including seizure disorder), stroke, significant bead injury, central nervous system tumors, or any other condition that predisposes patients to a risk for seizure.

Pre-assignment Details: A one-week single-blind placebo period was completed prior to randomization. Patients were then randomized in a 1:1 ratio to either, escitalopram or Composition-1

Method:

TABLE 7

| Arm | Intervention/treatment |
| --- | --- |
| Active Comparator: 1 Composition-1 (Fixed dose combination of (3R-3-acetyloxy-4-(trimethylazaniumyl) butanoate 500 mg + N-4-Aminobutylguanidine 250 mg) | Drug: Composition-1 ((3R)-3-acetyloxy-4-(trimethylazaniumyl)butanoate + N-4-aminobutylguanidine), oral administration, once capsule twice daily dosing for 12 weeks. |
| Active Comparator: 2 Escitalopram 20 mg | Drug: Escitalopram Escitalopram 20 mg, oral administration, once daily dosing for 12 weeks |

Study Design:

Baseline Characteristics

TABLE 8

| Arm/Group Title | Escitalopram | Composition-1 |
| --- | --- | --- |
| Arm/Group Description | Escitalopram high dose (20 mg) administered orally (QD [once a day]) for 12 weeks of stable dose treatment phase. The Overall Number of Baseline Participants is based on the Saftey population. | Composition-1, administered orally (BD [twice a day]) for 12 weeks of stable dose treatment phase. The Overall Number of Baseline Participants is based on the Safety population. |
| Started | 53 | 41 |
| Completed | 40 | 40 |
| Not Completed | 13 | 1 |
| Age Continuous Men (Standard Deviation) Unit of measure: Years | 40.4 (11.9) | 42.3 (12.7) |
| Sex: Female, Male Measure Type: Count of Participants Unit of measure: Participant | Female-28 (70%) Male-12 (30%) | Female-27 (68%) Male 13 (32%) |
| Drop Outs/Lost follow up (not considered for analysis) | 13 | 1 |
| Mean HAM-D Score at pretreatment | 26.2 | 25.72 |
| Mean serum ALCAR at pretreatment | 1.01 microgram/ml | 1.09 microgram/ml |

Study Outcome:
Primary Outcome Measures:
 Change From Baseline in Hamilton Rating Scale for Depression (HAM-D) at Week 4, 8 and 12 [Time Frame: Change from baseline in HAM-D at week 4, 8 and 12]
 The HAMD is a clinician-rated 21-item scale was used to rate the patient's depressive state. It was also used to identify obsessive-compulsive, genital, and somatic symptoms, as well as diurnal variation in the presence of symptoms. Each item was scored on a 1, 2, 3, 4 or 5-point Likert scale. A score of 0 indicated the absence of symptoms, and a score of 2, 3 or 4 indicated symptoms of maximum severity. The total score range is 0 to 62 (higher score indicates a greater depressive state).

Secondary Outcome Measures:
 To measure serum Acetyl-L carnitine levels pre-treatment and end of 12 weeks and correlate it with severity of depression and treatment outcomes.

Results

TABLE 9

| Outcome Measures | Treatment Arm | Baseline | Week-4 | Week-8 | Week-12 |
| --- | --- | --- | --- | --- | --- |
| Mean HAM-D Score | Escitalopram | 26.2 | 25.72 | 21.45 | 13.75 |
| | Composition-1 | 25.72 | 10.42 | 4.82 | 3.62 |
| Remission Rate (HAM-D Score <7) | Escitalopram | | 0/40 (0%) | 0/40 (0%) | 7/40 (17.5%) |
| | Composition-1 | | 10/40 (25%) | 35/40 (87.5%) | 35/40 (87.5%) |
| Responder Rate (50% Reduction from baseline) | Escitalopram | | 0/40 (0%) | 1/40 (2.5%) | 12/40 (30%) |
| | Composition-1 | | 26/40 (65%) | 1/40 (2.5%) | 2/40 (5%) |
| Non-Responder Rate | Escitalopram | | 40/40 (100%) | 39/40 (97.5%) | 21/40 (52.5%) |
| | Composition-1 | | 4/40 (10%) | 4/40 (10%) | 3/40 (7.5%) |
| Responder Remission Rate in Female Subgroup | Escitalopram | n = 28 | — | — | 7/28 (25%) |
| | Composition-1 | n = 27 | — | — | 27/27 (100%) |
| Non-Responder Remission Rate in Female Subgroup | Escitalopram | n = 28 | — | — | 21/28 (75%) |
| | Composition-1 | n = 27 | — | — | 0/27 (0%) |
| Mean Serum ALCAR (mcg/ml) | | | | | |
| Remission group (n-42) | Overall | 1.11 | — | — | 3.82 |
| | Escitalopram (n = 7) | 1.20 | — | — | 3.53 |
| | Composition-1 (n = 35) | 1.09 | — | — | 3.88 |
| Responder group (n = 14) | Overall | 1.09 | — | — | 2.40 |
| | Escitalopram (n = 12) | 0.91 | — | — | 2.19 |
| | Composition-1 (n = 2) | 1.20 | — | — | 2.57 |
| Non-Responder group (n = 24) | Overall | 0.96 | — | — | 0.99 |
| | Escitalopram (n = 21) | 0.94 | — | — | 0.99 |
| | Composition-1 (n = 3) | 1.04 | — | — | 1.05 |

Conclusions

Composition 1 significantly improved depression in female subjects over the marketed SSR1. The present composition is generally safe and well tolerated and did not worsen brain function.

The invention claimed is:

1. A method of treating depression, the method comprising:
   administering a unit dose of a bioactive composition twice daily to male and female subjects aged in a range of 18 to 65 years for a period of 12 weeks; and thereby
   wherein the unit dose of the bioactive composition comprises:
      a therapeutically active exogenous combination consisting of (3R)-3-acetyloxy-4-(trimethylazaniumyl) butanoate and N-(4-aminobutyl) guanidine or a salt thereof, wherein the (3R)-3-acetyloxy-4-(trimethylazaniumyl) butanoate is present in an amount of 500 mg and the N-(4-aminobutyl) guanidine or the salt thereof is present in an amount of 250 mg; and
      pharmaceutically acceptable excipients.

2. The method as claimed in claim 1, wherein the pharmaceutically acceptable excipients comprise a diluent, a binder, a lubricant, a glidant, an additive, a surfactant, a stabilizer, an antioxidant and a plasticizer; and wherein the diluent is present in a range of 1 to 30%; the binder is present in a range of 0.5 to 25%; the lubricant is present in a range of 0.1 to 10.0%; the glidant is present in a range of 0.1 to 5.0%; the additive is present in a range of 0.1 to 10%; the surfactant is present in a range of 0.1 to 5.0%; the stabilizer is present in a range of 0.1 to 5.0%; the antioxidant is present in a range of 0.1 to 5.0%; and the plasticizer is present in a range of 0.1 to 5.0%, each by weight of a total of the bioactive composition.

* * * * *